(12) United States Patent
Fuertes et al.

(10) Patent No.: US 8,283,009 B2
(45) Date of Patent: Oct. 9, 2012

(54) USE OF A MATERIAL BASED ON A THERMOPLASTIC POLYMER HAVING A HIGH CONTENT OF ANTIOXIDANTS FOR PACKAGING DIANHYDROHEXITOLS

(75) Inventors: Patrick Fuertes, Lomme (FR); Maxime Ingret, Bethune (FR); Anne Lambin, Lomme (FR); Herve Wyart, Cuinchy (FR)

(73) Assignee: Roquette Freres, Lestrem (FR)

( * ) Notice: Subject to any disclaimer, the term of this patent is extended or adjusted under 35 U.S.C. 154(b) by 447 days.

(21) Appl. No.: 12/671,753

(22) PCT Filed: Jul. 10, 2008

(86) PCT No.: PCT/FR2008/051296
§ 371 (c)(1),
(2), (4) Date: Feb. 2, 2010

(87) PCT Pub. No.: WO2009/019371
PCT Pub. Date: Feb. 12, 2009

(65) Prior Publication Data
US 2011/0233102 A1    Sep. 29, 2011

(30) Foreign Application Priority Data
Aug. 2, 2007 (FR) ...................................... 07 05653

(51) Int. Cl.
*B29D 22/00* (2006.01)
*B29D 23/00* (2006.01)
*B32B 1/08* (2006.01)

(52) U.S. Cl. ....... 428/35.7; 428/500; 53/467; 206/524.6
(58) Field of Classification Search ................. 428/35.7, 428/500; 206/524.6; 53/467
See application file for complete search history.

(56) References Cited

U.S. PATENT DOCUMENTS
2004/0110969 A1    6/2004   Fleche et al.

FOREIGN PATENT DOCUMENTS
| | | |
|---|---|---|
| EP | 1 287 000 B | 10/2005 |
| JP | 2006 117649 A | 5/2006 |
| WO | 03/043959 A | 5/2003 |

OTHER PUBLICATIONS

Database WPI Week 200634, Thomson Scientific, London, GB; AN 2006-324989, XP002473828.
International Search Report in Corresponding Application PCT/FR2008/051296 Dated Feb. 3, 2009.

*Primary Examiner* — Michael C Miggins
(74) *Attorney, Agent, or Firm* — Young & Thompson

(57) ABSTRACT

The present invention relates to the use of a packaging material based on a thermoplastic polymer for packaging a dianhydrohexitol, the packaging material comprising at least one thermoplastic polymer layer containing at least 0.1% by weight of at least one antioxidant (layer (A)), said layer (A) either being directly in contact with the dianhydrohexitol or being separated from the latter by a thermoplastic polymer layer (layer (B)) having a thickness at most equal to 150 μm, and the thermoplastic polymer of the layer (A) and/or of the layer (B) being chosen independently from polyethylene, polypropylene, ethylene/polypropylene copolymers and blends of the latter.

18 Claims, No Drawings

USE OF A MATERIAL BASED ON A THERMOPLASTIC POLYMER HAVING A HIGH CONTENT OF ANTIOXIDANTS FOR PACKAGING DIANHYDROHEXITOLS

The present invention relates to the use of a particular thermoplastic material containing a layer having a high content of antioxidants, for packaging dianhydrohexitols.

Dianhydrohexitols, also known as isohexides, are products of internal dehydration of $C_6$ hydrogenated sugars (hexitols) such as sorbitol, mannitol and iditol.

Among these doubly dehydrated hydrogenated sugars, isosorbide is today the one for which the most industrial applications are developed and envisaged to be developed, especially in the pharmaceutical field, in the field of chemical synthesis intermediates and in the field of plastics.

For the majority of these applications, it is generally necessary to have compositions that are as pure as possible, in particular that have a dianhydrohexitol content at least equal to 98.5% by weight, preferably at least equal to 99.5% by weight.

The observation that dianhydrohexitols, and in particular isosorbide, were products that are not only highly hygroscopic but are chemically not very stable is a relatively recent one.

The Applicant has in particular observed that the storage of isosorbide manufactured according to known processes, even protected from atmospheric moisture, could lead under certain temperature conditions to a chemical degradation resulting, inter alia, in the formation of formic acid, which acid has a characteristic and unpleasant odor that is particularly annoying in pharmaceutical applications or other applications.

The Applicant was thus led to develop processes for purifying and stabilizing dianhydrohexitols that are described, in particular, in Patent Applications EP 1 287 000 and WO 03/043959.

Within the context of the research that led to the inventions disclosed in these applications, the stability of the products was evaluated by storing samples to be tested in a container, respectively made of plastic (EP 1 287 000) or made of glass (WO 03/043959), at a thermostatted temperature equal to, respectively, 60° C. or 40° C. These stability tests thus made it possible to predict the storage stabilities of the products sold by the Applicant.

It is only very recently that the Applicant became aware of the fact that the shelf lives of dianhydrohexitols, determined under the conditions of the stability tests described in Applications EP 1 287 000 and WO 03/043959, only imperfectly reflected the stability of these same products under the actual transport and storage conditions. The Applicant has revealed, in particular in some cases, relatively higher concentrations of formic acid in the vicinity of the polyethylene packaging film. This locally high concentration could suggest that the degradation of isosorbide, and of dianhydrohexitols in general, did not take place only according to an intrinsic, temperature-dependent kinetic pathway, but was also linked, inter alia, to the interaction with the packaging material.

This discovery was at the very least surprising. Indeed, polyethylene, a plastic that is universally used for the packaging of technical, pharmaceutical and food products, has the reputation of being a stable, inert and inoffensive material. Replacing it with a different plastic poses a certain number of problems: specifically, polyethylene is among the cheapest polymers on the market and has, inter alia, an excellent heat sealability. The latter characteristic may prove essential for the packaging of hygroscopic and/or chemically unstable products such as dianhydrohexitols, which are preferably stored in hermetic packagings that are impermeable to oxygen and to water vapor.

The Applicant has therefore set itself the objective of finding an inexpensive and heat-sealable plastic that makes it possible to package high-purity dianhydrohexitol compositions and which, unlike conventional polyethylene, does not accelerate the chemical degradation of dianhydrohexitols.

Patent Application JP 2006-117649 discloses the use of a film-type packaging material for packaging isosorbide for the purpose of protecting the latter against absorption of water, of keeping it in the form of a fluid powder and of preventing the formation of aggregates. The packaging film is defined very vaguely as being a multilayer film based on plastics and on aluminum. Moreover, this document does not mention the problem of the chemical instability of dianhydrohexitols in contact with the packaging material.

In the context of its research targeting the development of such a packaging material or the selection thereof from known packaging materials, the Applicant has surprisingly observed that it was possible to considerably improve the stability of dianhydrohexitols, and in particular of isosorbide, by substantially increasing the antioxidant concentration of the layer of plastic in contact with the product. The Applicant has moreover made the discovery, even more surprisingly, that the incorporation of such an amount of antioxidant had a stabilizing effect not only when the antioxidant was in the layer directly in contact with the product, but also when it was introduced into the layer immediately adjacent to the layer in contact with the product, on the condition that the latter does not have an excessive thickness.

One subject of the present invention is consequently a dianhydrohexitol packaged in a packaging material based on a thermoplastic polymer, characterized by the fact that the packaging material comprises at least one layer of thermoplastic polymer containing at least 0.1% by weight, preferably at least 0.2% by weight, of at least one antioxidant (layer (A)), said layer (A) either being directly in contact with the dianhydrohexitol or being separated from the latter by a supplementary layer made from a thermoplastic polymer (layer (B)) having a thickness at most equal to 150 μm, preferably at most equal to 120 μm, and by the fact that the thermoplastic polymer of the layer (A) and/or of the layer (B) is chosen independently from polyethylene, polypropylene, copolymers of ethylene and of propylene, and mixtures thereof.

In addition, one subject of the invention is the use of such a packaging material based on a thermoplastic polymer for packaging a dianhydrohexitol, or else a process for packaging a dianhydrohexitol, comprising the introduction of said dianhydrohexitol into a packaging made from such a material, and the sealing of said packaging.

Dianhydrohexitols (1,4:3,6-dianhydrohexitols) encompass isosorbide (1,4:3,6-dianhydrosorbitol), isomannide (1,4:3,6-dianhydromannitol), isoidide (1,4:3,6-dianhydroiditol) and mixtures of at least two of these products. Preferably, the packaged dianhydrohexitol according to the present invention comprises isosorbide or is essentially constituted of isosorbide. It is preferably a composition for which the isosorbide content is at least equal to 98.5% by weight (dry weight/dry weight).

Although the utility of the present invention applies in principle to both solid and liquid compositions of dianhydrohexitols, it is particularly important for the solid forms.

As solid forms, these may be, for example, cooled and solidified distillates or crystals, all of these products possibly, in particular, being in the form of a powder or flakes.

The use of a plastic as defined in the present application for the packaging of dianhydrohexitols in solid form, and especially in anhydrous crystalline form, consequently constitutes one preferred embodiment of the present invention.

The term "antioxidant" used in the present invention encompasses all the compounds capable of limiting or eliminating thermooxidative degradation, also known by the term autoxidation, of organic compounds, in particular of organic polymers.

A non-exhaustive list of these compounds is given in chapter 1, entitled "Antioxidants", of the fifth edition of the work "Plastics Additives Handbook" (2001), Carl Hanser Verlag, Munich (Germany).

Among the preferred antioxidant compounds, mention may be made of:
- hydrogen donors such as secondary aromatic amines and highly sterically hindered phenols;
- the decomposition agents of hydroperoxides based on phosphorus such as phosphites and phosphonites, and those based on sulfur such as 3,3-thiodipropionic acid esters; and
- free-radical scavengers such as carbon black, highly sterically hindered amines, hydroxylamines, benzofuranone derivatives and phenols modified by acryloyl groups.

Hydrogen donors of phenol type encompass, for example, those bearing the following CAS numbers: 10191-41-0 (tocopherol), 128-37-0, 2082-79-3, 12643-61-0, 119-47-1, 35074-77-2, 23128-74-7, 976-56-7, 65140-91-2, 36443-68-2, 85-60-9, 90498-90-1, 1709-70-2, 1843-03-4, 34137-09-2, 27676-62-6, 40601-76-1, 6683-19-8, 32509-66-3, 31851-03-3, 134701-20-5, 96-69-5, 90-66-4, 110553-27-0, 41484-35-9, 991-84-4, 103-99-1, 63843-89-0, 4221-80-1, 67845-93-6, 136-36-7, 61167-58-6, 128961-68-2, 181314-48-7, 143925-92-2, 135-88-6, 26780-96-1, 101-72-4, 90-30-2, 68411-46-1, 10081-67-1 and 118832-72-7.

The decomposition agents of hydroperoxides of phosphite or phosphonite type encompass, for example, those bearing the following CAS numbers: 26523-78-4, 31570-04-4, 26741-53-7, 80693-00-1, 140221-14-3, 119345-01-6/38613-77-3, 118337-09-0, 3806-34-6, 80410-33-9, 145650-60-8, 161717-32-4 and 154862-43-8. The decomposition agents of hydroperoxides based on sulfur encompass the compounds bearing the following CAS numbers: 693-36-7, 123-28-4, 16545-54-3 and 2500-88-1.

The highly sterically hindered amines encompass the compounds bearing the following CAS numbers: 52829-07-9, 65447-77-0, 71878-19-8, 106990-43-6, 41556-26-7, 63843-89-0, 129757-67-1, 192268-64-7, 90751-07-8, 219920-30-6, 79720-19-7, 106917-30-0, 24860-22-8, 131290-28-3, 109-423-00-9, 124172-53-8, 199-237-39-3, 91788-83-9, 64022-61-3, 107119-91-5, 100631-43-4, 115055-30-6, 100631-44-5, 95078-42-5, 85099-51-1/85099-50-9, 78276-66-1, 76505-58-3, 136504-96-6, 71029-16-8, 96204-36-3, 130277-45-1, 85099-51-0, 147783-69-5, 154636-12-1, 84214-94-8, 99473-08-2, 164648-93-5 and 42774-15-2.

In one particularly preferred embodiment of the present invention, the antioxidant comprises carbon black or is essentially constituted of carbon black. This carbon black must advantageously have a sufficiently fine particle size in order to be able to be incorporated homogeneously into the layer (A). The most suitable particle size of the carbon black therefore depends in particular on the thickness of the layer (A).

Whether it is carbon black or another antioxidant chosen from those indicated in the Plastics Additives Handbook referenced above, the concentration of the antioxidant is preferably between 0.1 and 10% by weight, in particular between 0.2 and 5% by weight and more preferably still between 0.3 and 3% by weight.

As indicated above, the layer (A) containing the antioxidant may be directly in contact with the dianhydrohexitol. In this embodiment, it is particularly recommended to make sure that the particle size of said antioxidant, in particular of the carbon black, is relatively small compared to the thickness of the layer (A). It is indeed particularly advantageous for the particles of said antioxidant, in particular of the carbon black, to be perfectly incorporated into the layer of polyethylene, of polypropylene and/or of copolymers of ethylene and of propylene, in such a way that the internal surface of the packaging is smooth and does not comprise projecting particles that are capable of coming off or breaking and thus polluting the packaged product.

In a second embodiment, the layer (A) containing the antioxidant is separated from the dianhydrohexitol by a layer (B) made of a thermoplastic polymer, that is free of antioxidant or that has an antioxidant content of less than 0.1% by weight, preferably less than 0.05% by weight.

This supplementary layer (B), inserted between the dianhydrohexitol and the layer (A) filled with antioxidant, is preferably essentially constituted of polyethylene (PE), polypropylene (PP), copolymers of ethylene and propylene (PE/PP) or mixtures thereof.

According to one advantageous variant, the layer (B) is a polyethylene layer that is not filled with carbon black and which is directly in contact with the dianhydrohexitol.

This layer (B) may however be a multilayer type structure, itself constituted of two or more layers, one or more of which are based on PE, PP, PE/PP or a mixture thereof, and optionally one or more other layers based on a different thermoplastic polymer.

Of course, the indications concerning the thickness of the layer (B) of the packaging used in the present invention concern either the thickness of the single-layer structure, or, where appropriate, the total thickness of the assembly of the layers forming the multilayer structure.

As indicated in the introduction, this thickness of the layer (B), whether it is single-layer or multilayer, should not exceed 150 μm. Beyond this maximum value, the stabilizing effect of the antioxidant present in the adjacent layer (A) actually becomes insufficient. The layer (B) preferably has a thickness at most equal to 120 μm, advantageously between 10 and 100 μm, and in particular between 15 and 50 μm.

As indicated above, the packaging material of the present invention comprises at least one layer based on PE, PP, PE/PP or on a mixture thereof. These polymers or combinations of polymers are chosen owing to their excellent heat sealability, their low cost and their wide availability.

The thermoplastic polymer of the layer (A) and/or of the layer (B) is preferably polyethylene. It is in particular branched polyethylene, obtained by radical polymerization, linear polyethylene, prepared by Ziegler-Natta polymerization, and/or metallocene polyethylene, obtained by zinc/zirconium-catalyzed polymerization.

According to one preferred embodiment of the present invention, the layer (A) is made from polyethylene filled with carbon black and the layer (B) is made from polyethylene that is not filled with carbon black and is directly in contact with the dianhydrohexitol.

In another preferred embodiment, the dianhydrohexitol is hermetically packaged, that is to say that the packaging, for example the sachet, liner or pouch or bag, containing the dianhydrohexitol is sealed, for example by heat sealing or by means of a suitable tie, so as to limit as much as possible, and if possible to eliminate, any exchange of gas between the inside of the packaging and the surrounding air. The leak-tightness of the packaging is particularly important for isosorbide which, in the solid state, is an extremely hygroscopic product.

Under certain conditions, it may be advantageous to package the dianhydrohexitol under an anhydrous and/or inert atmosphere, for example under a nitrogen atmosphere.

In order to guarantee optimal stability of the dianhydrohexitol during transport and storage, it may sometimes be useful, or even necessary, to provide a supplementary layer of partial or total protection against oxygen from the air, water vapor and/or light. Such a barrier layer that is not very permeable, or even impermeable, to water vapor and to oxygen (layer (C)), and preferably also to light, is preferably located on the outside of the layer (A), that is to say that it is not inserted between the layer (A) and the packaged product. This layer (C) is preferably in direct contact with the outer surface of the layer (A).

Mention may be made, by way of examples of such barrier layers (C), of layers based on an ethylene/vinyl alcohol copolymer ("EVOH"), on polyvinylidene chloride ("PVDC"), on polyamide ("PA"), on polyacrylonitrile ("PAN") and/or on polyglycolic acid ("PGA"). The barrier layer (C) may also be a deposition of aluminum and/or of another suitable metal, deposited, for example, on the outer surface of the layer (A), or a sheet of aluminum and/or of another suitable metal, preferably in direct contact with the outer surface of the layer (A).

The overall thickness of the packaging does not play a determining role in the present invention. It may indeed be a thin and flexible material, for example of film or sheet type, the thickness of which does not exceed a few tens or a few hundreds of microns, but also a more rigid material in the form of a container having a given shape. Mainly for cost reasons, the packaging material preferably has a total thickness at most equal to 300 µm. A packaging material according to the invention having a total thickness between 30 and 250 µm generally makes it possible to achieve a satisfactory compromise between sufficient mechanical solidity and production cost. The packaging may then advantageously be in the form of sachets, liners or pouches or bags of any shapes, dimensions and capacities and for example in the form of a liner or pouch which, in view of the transport or storage of dianhydrohexitol, may already be contained or may be intended to be contained in a flexible container such as an aluminum bag or a "big-bag" or "flexible intermediate container" (FIS) made of cloth or woven fabric, or in a rigid container such as a cardboard box.

The Applicant has, in particular, obtained excellent results, in terms of storage stability, with a film having a total thickness of less than 150 µm, comprising a layer (A) made of polyethylene filled with 2% by weight approximately of carbon black and a layer (B) made of polyethylene containing less than 0.05% by total weight of antioxidants and in particular that is free of carbon black, directly in contact with the dianhydrohexitol. Owing to the internal polyethylene coating (layer (B)), the film is easy to weld with conventional heat-sealing machines and there is no risk of contamination of the packaged product by carbon black.

The superiority of such a packaging film over four conventional polyethylene films, containing less than 0.05% by total weight of antioxidants and in particular that is free of carbon black, is illustrated in the example below which has a purely illustrative nature.

EXAMPLE 1

50 g of isosorbide in solid form (flakes) are introduced into a sachet (25 cm×25 cm) constituted of the packaging material to be tested. The sachet is immediately sealed by welding using an impulse heat sealer (model SZ 380 sold by Joisten & Kettenbaum GmbH & Co, Bergisch Gladbach, Germany). The thus sealed sachet is in turn introduced into a second sachet made of aluminum comprising a polyethylene coating, sealed by welding using the same heat sealer in order to ensure leaktightness with respect to the external atmosphere. The samples thus packaged are placed in a ventilated oven, thermostatted at a temperature of 50° C. A control sample is enclosed in a glass flask and stored under the same conditions.

After a given period, the whole of the sample of isosorbide is extracted from the packagings and dissolved to 40% by weight of solids in osmosed water. The pH of the solution is measured for each sample.

The pH-metry results are presented in table 1 below.

TABLE 1

Storage stability of isosorbide in different polyethylene-based packaging films

| Storage duration | PE + carbon black (according to the invention) | Sachet 1 (comp.) R*/L* (50%/50%) | Sachet 2 (comp.) R*/L* (70%/30%) | Sachet 3 (comp.) 100% of R* | Sachet 4 (comp.) 100% of L* |
|---|---|---|---|---|---|
| 0 day | pH 7.6 | pH 7.6 | pH 7.6 | pH 7.6 | pH 7.6 |
| 2 weeks | pH 7.2 | pH 7.5 | pH 7.5 | pH 3.6 | pH 7.2 |
| 1 month | pH 7.3 | pH 7.4 | pH 3.1 | | pH 2.9 |
| 1.5 month | pH 7.4 | pH 7.4 | | | |
| 2 months | pH 7.5 | pH 3.0 | | | |
| 2.5 months | pH 7.5 | | | | |
| 3 months | pH 7.6 | | | | |
| 4 months | pH 7.7 | | | | |

R* = branched polyethylene;
L* = linear polyethylene

The pH of the control sample, stored in a glass container, as a whole remains stable (pH varying between 7.2 and 7.7) up to 3 months. However, after 4 months of storage, a very significant drop in the pH, which falls to a value of 3.0, is measured.

These examples clearly show the superiority of the packaging film that can be used according to the invention compared to the four conventional polyethylene films, containing low contents of antioxidants and that are free of carbon black, and even compared to the glass packaging.

All of the samples that were not packaged in accordance with the invention had after 4 months (glass packaging), or even after only 2 months (sachet 1), 1 month (sachets 2 and 4) or even 2 weeks (sachet 3), a pH significantly below 4 and a characteristic odor of formic acid.

Conversely, the isosorbide packaged in accordance with the invention exhibited no drop in pH after 4 months of storage. An analysis carried out at that time on the packaged product did not show any presence of peroxides, that is to say of markers of oxidation phenomena, and therefore of instability.

The invention claimed is:

1. A dianhydrohexitol packaged in a packaging material based on a thermoplastic polymer, wherein the packaging material comprises at least one layer of thermoplastic polymer containing at least 0.1% by weight of at least one antioxidant (layer (A)), said layer (A) either being directly in contact with the dianhydrohexitol or being separated from the latter by a layer made from a thermoplastic polymer (layer (B)) having a thickness at most equal to 150 µm and by the fact that the thermoplastic polymer of the layer (A) and/or of the layer (B) is chosen independently from polyethylene, polypropylene, copolymers of ethylene and of propylene, and mixtures thereof.

2. The packaged dianhydrohexitol as claimed in claim 1, said dianhydrohexitol being in solid form.

3. The packaged dianhydrohexitol as claimed in claim 1, wherein the layer of thermoplastic polymer contains at least 0.2% by weight of at least one antioxidant.

4. The packaged dianhydrohexitol as claimed in claim 1, wherein the layer (B) has a thickness at most equal to 120 μm.

5. The packaged dianhydrohexitol as claimed in claim 1, wherein the layer (B) has a thickness of between 10 and 100 μm.

6. The packaged dianhydrohexitol as claimed in claim 1, wherein the dianhydrohexitol comprises isosorbide or essentially consists of isosorbide.

7. The packaged dianhydrohexitol as claimed in claim 1, wherein the thermoplastic polymer of the layer (A) and/or of the layer (B) is polyethylene, preferably branched polyethylene, linear polyethylene and/or metallocene polyethylene.

8. The packaged dianhydrohexitol as claimed in claim 1, wherein the antioxidant is carbon black.

9. The packaged dianhydrohexitol as claimed in claim 1, wherein the packaging material comprises a layer (A) made from polyethylene filled with carbon black and a layer (B) made from polyethylene that is not filled with carbon black, directly in contact with the dianhydrohexitol.

10. The packaged dianhydrohexitol as claimed in claim 1, wherein the packaging material also comprises a barrier layer that is not very permeable or that is impermeable to water vapor and to oxygen (layer (C)), located on the outside of the layer (A).

11. The packaged dianhydrohexitol as claimed in claim 1, wherein the dianhydrohexitol is hermetically packaged.

12. The packaged dianhydrohexitol as claimed in claim 11, wherein the dianhydrohexitol is packaged under an inert atmosphere.

13. The packaged dianhydrohexitol as claimed in claim 1, wherein the packaging material based on a thermoplastic polymer has a total thickness at most equal to 300 μm.

14. The packaged dianhydrohexitol as claimed in claim 13, wherein the packaging material based on a thermoplastic polymer has a total thickness of between 30 and 250 μm.

15. The packaged dianhydrohexitol as claimed in claim 1, wherein the layer (A) contains from 0.1 to 10% by weight of antioxidant.

16. The packaged dianhydrohexitol as claimed in claim 15, wherein the layer (A) contains from 0.2 to 5% by weight of antioxidant.

17. The packaged dianhydrohexitol as claimed in claim 16, wherein the layer (A) contains from 0.3 to 3% by weight of antioxidant.

18. A process for packaging dianhydrohexitol, comprising the introduction of said dianhydrohexitol into a packaging made from a material based on a thermoplastic polymer, and the sealing of said packaging, said process being characterized by the fact that the packaging material comprises at least one layer of thermoplastic polymer containing at least 0.1% by weight of at least one antioxidant (layer (A)), said layer (A) either being directly in contact with the dianhydrohexitol or being separated from the latter by a layer made from a thermoplastic polymer (layer (B)) having a thickness at most equal to 150 μm, and by the fact that the thermoplastic polymer of the layer (A) and/or of the layer (B) is chosen independently from polyethylene, polypropylene, copolymers of ethylene and of propylene, and mixtures thereof.

* * * * *